United States Patent
Da Silva et al.

(10) Patent No.: US 8,120,784 B2
(45) Date of Patent: Feb. 21, 2012

(54) OPTICAL DEVICE FOR ANALYZING A SCATTERING MEDIUM HELD BY A SUPPORT

(75) Inventors: Anabela Da Silva, Marseilles (FR); Philippe Rizo, La Tronche Cedex (FR); Michel Berger, Claix (FR); Laurent Guyon, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 410 days.

(21) Appl. No.: 12/425,558

(22) Filed: Apr. 17, 2009

(65) Prior Publication Data

US 2009/0262365 A1 Oct. 22, 2009

(30) Foreign Application Priority Data

Apr. 18, 2008 (FR) ...................... 08 82633

(51) Int. Cl.
*G01B 11/30* (2006.01)
*G01B 11/24* (2006.01)
(52) U.S. Cl. ........................ 356/601; 356/608
(58) Field of Classification Search ........... 356/600–640
See application file for complete search history.

(56) References Cited

U.S. PATENT DOCUMENTS

| | | | | |
|---|---|---|---|---|
| 5,396,895 | A * | 3/1995 | Takashima et al. | 600/500 |
| 6,181,958 | B1 * | 1/2001 | Steuer et al. | 600/322 |
| 6,353,226 | B1 * | 3/2002 | Khalil et al. | 250/341.8 |
| 6,475,800 | B1 * | 11/2002 | Hazen et al. | 436/8 |
| 2004/0039379 | A1 * | 2/2004 | Viator et al. | 606/9 |
| 2005/0030372 | A1 * | 2/2005 | Jung et al. | 348/77 |

FOREIGN PATENT DOCUMENTS

| | | |
|---|---|---|
| EP | 0147124 A | 7/1985 |
| WO | 99/40411 A | 8/1999 |
| WO | 0242824 A | 5/2002 |
| WO | 02/095476 A | 11/2002 |
| WO | 2007/057798 A | 5/2007 |

OTHER PUBLICATIONS

Yang et al, "Determination of human skin optical properties in vivo from reflectance spectroscopic measurements" Chinese Optics Letters col. 5, No. 3, Mar. 10, 2007, pp. 181-183.*
Jacques, Steven. Optical properties of "Intralipid™" an aqueous suspension of lipid droplets, Oregon Medical Laser Center, Apr. 1, 1998. http://omlc.ogi.edu/spectra/intralipid/index.html.*
European Search Report issued in EP 09158148 on Jul. 14, 2009.
"French Search Report" issued Dec. 9, 2008 for Application FR 08/52633.
"Performance of Different Reflectance and Diffuse Optical Imaging Tomographic Approaches in Fluorescence Molecular Imaging of Small Animals", J.M. Dinten, et al., Proceedings of Spie. Medical Imaging 2006: Physics of Medical Imaging, vol. 6142, 2006.
"Optical Projection Tomography" J. Sharpe, Annual Rev Biomed Eng. vol. 6, Apr. 9, 2004.

* cited by examiner

*Primary Examiner* — Gregory J Toatley
*Assistant Examiner* — Jarreas C Underwood
(74) *Attorney, Agent, or Firm* — Vedder Price PC

(57) ABSTRACT

An optical device intended for the analysis of a scattering medium, including at least one light source distant from the scattering medium and capable of providing an incident light beam intended to illuminate the scattering medium; at least one sensor capable of detecting a radiation emitted by the scattering medium; a support of the scattering medium at least partially non-absorbing for the incident light beam and the scattered radiation. All or part of the support is formed of a scattering material having a decreased scattering coefficient greater than 0.1 cm$^{-1}$ and smaller than 700 cm$^{-1}$.

11 Claims, 2 Drawing Sheets

OPTICAL DEVICE FOR ANALYZING A SCATTERING MEDIUM HELD BY A SUPPORT

BACKGROUND OF THE INVENTION

1. Field of the Invention

The present invention relates to an optical device for analyzing a scattering medium held by a support.

2. Discussion of the Related Art

A subject area of optical imaging relates to the analysis of a scattering medium, for example, the analysis of biological tissues.

Generally, the scattering medium is submitted to an incident light beam. For certain applications, for example, in optical diffusion tomography, the wavelength of the incident beam is in the visible spectrum, conventionally in the red or in the near infrared, which corresponds to the wavelength range where the absorption of the biological tissues is minimum. The incident light beam scatters into the scattering medium and the scattered light radiation which escapes from the scattering medium is detected by a sensor, for example, a camera. The images provided by the sensor are analyzed to determined the optical properties of the scattering medium, for example, to determine the distribution of the optical diffusion and/or absorption properties of the scattering medium, for example, to detect the presence of an abnormally absorbing and/or scattering area.

For other applications, for example, in fluorescence optical diffusion tomography, specific fluorescent tags which tend to concentrate in areas of interest are arranged in the scattering medium. When they are illuminated by the incident light beam, the tags emit a radiation at a wavelength distinct from that of the incident beam. This radiation scatters into the scattering medium and is detected and analyzed to determine the properties of the tags (for example, the location and the local concentration of the tags).

In the field of medical imaging, optical imaging techniques provide, for example, to detect and locate carcinomae, an alternative to conventional imaging techniques such as radiography and X-ray laminography, positron emission tomography, magnetic resonance imaging, etc.

For certain optical devices, the light source is in direct contact with the scattering medium. As an example, the incident light beam is guided all the way to the scattering medium by optical fibers. The scattered radiation emitted by the scattering medium may also be collected by optical fibers and guided all the way to the sensor. An advantage is that the environment of the scattering medium, in particular the support holding the scattering medium, does not disturb the measurements. However, such optical devices are generally bulky since the accessible accuracy of the distribution of the optical properties depends on the number of independent measurements that may be performed, that is, on the number of optical fibers used.

For other optical devices, the light source is distant from the scattering medium. The structure of the optical device can then be simplified. The support holding the scattering medium is generally designed to disturb as little as possible the propagation of light rays. For this purpose, the support is formed of a material non-absorbing and non-scattering for the useful wavelength range.

FIGS. 1 and 2 show two embodiments of optical devices for which the light source is distant from the scattering medium. Each optical device 10, 12 comprises a light source 14, for example, a laser diode providing a monochromatic light beam 15 having a wavelength of, for example, 670 nanometers, and an image sensor 16 adapted to the detection of a scattered radiation. An analysis tool 17 is connected to sensor 16 and processes the images acquired by sensor 16. A scattering medium to be analyzed 18, for example, a mouse, is arranged to receive incident light beam 15 provided by light source 14. A lens 19 is arranged between scattering medium 18 and sensor 16. It is possible for the axis of sensor 16 not to be parallel to incident beam 15. According to a variation, the images provided by sensor 16 may be recorded by tool 17 and subsequently analyzed by means of another computer.

For device 10 shown in FIG. 1, medium 18 to be analyzed is held by a support 20 comprising an input plate 22 located between medium 18 and light source 14 and an output plate 24 located between medium 18 and sensor 16. Plates 22, 24 are transparent and parallel. As an example, support 20 may be fixed and light source 14 may be mobile with respect to support 20. For device 12 shown in FIG. 2, medium 18 to be analyzed is held by a support 30 corresponding to a transparent tube comprising a cylindrical lateral wall 32 and a planar bottom 34. As an example, support 20 is mounted on a rotating arm 38, while source 14 may be fixed.

Support 20, 30 is generally made of plastic or glass. However, the use of such supports may result in the forming of artifacts on the images provided by sensor 16. Such artifacts may disturb, or even hinder the analysis of scattering medium 18.

SUMMARY OF THE INVENTION

The present invention aims at an optical device for analyzing a scattering medium held by a support comprising a light source and a sensor, the light source being distant from the medium to be analyzed, the support enabling to decrease, or even to suppress, the forming of artifacts on the images acquired by the sensor.

Another feature of the support is that it can be made in a simple way.

Another feature is that the optical properties of the support vary little along time.

Thus, an embodiment of the present invention provides an optical device intended for the analysis of a scattering medium. The device comprises at least one light source distant from the scattering medium and capable of providing an incident light beam intended to illuminate the scattering medium; at least one sensor capable of detecting a radiation emitted by the scattering medium; a support of the scattering medium at least partially non-absorbing for the incident light beam and the scattered radiation. All or part of the support is formed of a scattering material having a decreased scattering coefficient greater than 0.1 cm$^{-1}$ and smaller than 700 cm$^{-1}$.

According to an embodiment of the present invention, the scattering coefficient ranges between 1 and 700 cm$^{-1}$.

According to an embodiment of the present invention, said material has an absorption coefficient ranging between 0.01 and 300 cm$^{-1}$.

According to an embodiment of the present invention, the support comprises at least one wall intended to be located between the source and the scattering medium and/or between the scattering medium and the sensor.

According to an embodiment of the present invention, the support has the shape of a cradle intended to receive the scattering medium.

An embodiment of the present invention provides a support adapted to the previously-described optical device.

An embodiment of the present invention provides a use of the previously-described optical device, to form by tomography a three-dimensional mapping of the absorption coefficient and/or of the decreased scattering coefficient of the scattering medium.

An embodiment of the present invention provides a use of the previously-described optical device, the incident light beam being at a first wavelength, the use comprising the placing in the scattering medium of fluorophores sensitive to the first wavelength and emitting the scattered radiation at a second wavelength, the sensor providing images used to determine properties of the fluorophores and/or properties of the scattering medium.

An embodiment of the present invention provides a method for manufacturing the previously-described support. The method comprises the steps of preparing a powder of a scattering material; mixing the powder with a solution of a substantially non-absorbing, non-scattering, and hardenable material; and injecting the obtained mixture into a mold to form the support.

According to an embodiment of the present invention, the method further comprises the step of mixing an additional solution of an absorbing material with the powder or with the solution.

The foregoing objects, features, and advantages of the present invention will be discussed in detail in the following non-limiting description of specific embodiments in connection with the accompanying drawings.

DETAILED DESCRIPTION

Figure 1:
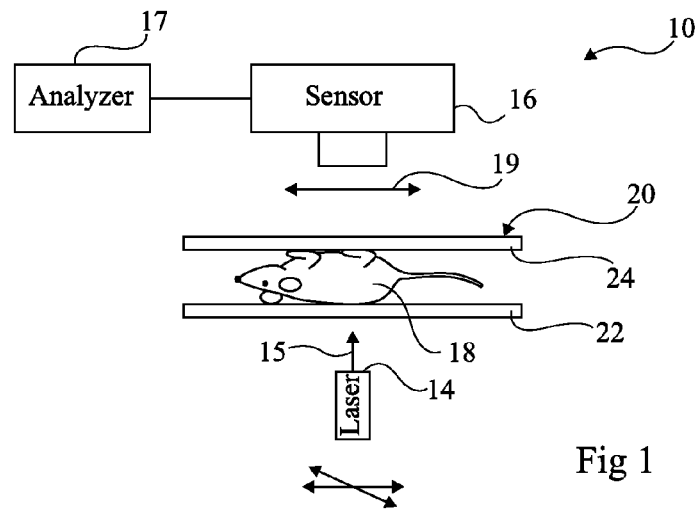
FIGS. 1 and 2, previously described, schematically show conventional examples of optical devices for analyzing a scattering medium.

For clarity, the same elements have been designated with the same reference numerals in the different drawings.

The Applicant has come to the present invention by an analysis of the phenomena causing the forming of artifacts on the images delivered by the sensor of an optical device for the analyzing a scattering medium.

Figure 2:
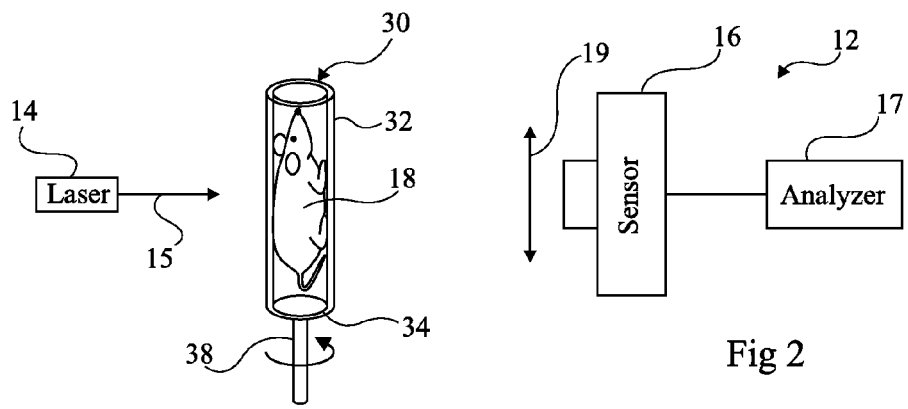
Figure 3:
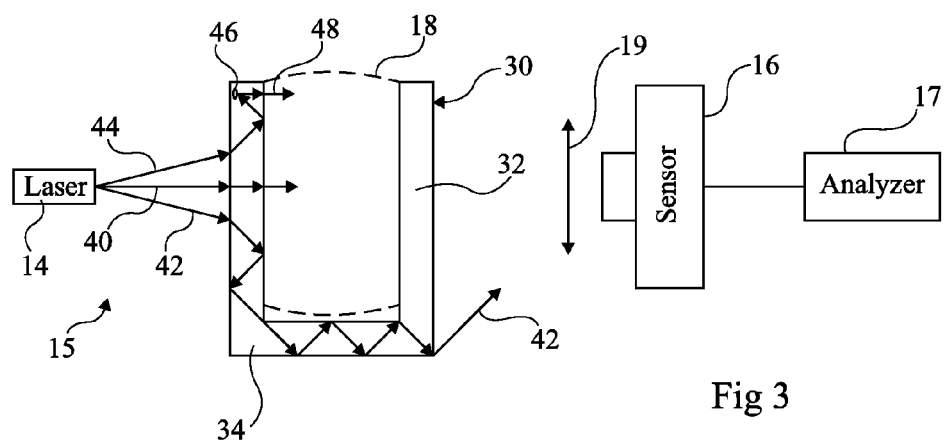
FIG. 3 schematically illustrates artifacts that can be observed with the device of FIG. 2.

FIG. 3 schematically illustrates phenomena causing the forming of artifacts that may be observed on the images acquired by sensor 16 of device 12 of FIG. 2. In FIG. 3, support 30 is shown in lateral cross-section view. Incident light beam 15 exhibits a beam angle, and a light ray 40 of incident beam 15 substantially perpendicular to wall 32 and rays 42, 44 of incident beam 15 inclined with respect to the axis of wall 32 have been schematically shown. Light ray 40 crosses support 30 undisturbed to reach scattering medium 18 to be analyzed.

A first type of artifact results from light rays which directly reach sensor 16 without having crossed the medium to be analyzed. This may result from an optical guiding of oblique rays 42, 44 by the walls of support 30. As an example, oblique rays 42 may be guided by lateral wall 32 and bottom 34 of support 30, and then escape from support 30 and directly reach sensor 16 without having crossed scattering medium 18. The intensity of light rays 42 which directly reach sensor 16 may be much greater than that of the scattered radiation. Sensor 16 being generally adapted to the detection of a low-intensity scattered radiation, the fact for light rays 42 to directly reach sensor 16 may result in a saturation thereof, which makes the acquired images impossible to use. It could be considered that the previously-described phenomena are not penalizing for the fluorescence optical diffusion tomography of the incident light beam. However, the fluorescence optical diffusion tomography may also use the image of the scattered radiation emitted by the scattering medium at the wavelength of the incident beam for calibration purposes.

A second type of artifact results from defects 46 (inclusions, scratches, cracks, etc.) of support 30. Indeed, when light rays 44, optically guided by wall 32, reach defect 46, the latter may emit, by reflection, refraction, or diffraction, a light beam 48. Defect 46 is then equivalent to a parasitic light source contributing to the radiation emitted by the scattering medium. This second type of artifacts may be as penalizing as the first type of artifact since it disturbs the analysis of the detected images, given that the algorithms for processing the images provided by sensor 16 are based on the assumption that the properties of the illumination of scattering medium 18 are well-known, where this illumination may result from a single source 14, from several point light sources, from non-point sources, etc. Further, since the distribution of the parasitic sources is not known, taking them into account to be difficult. This type of artifact may also occur for optical device 10 shown in FIG. 1.

The present invention provides using a scattering material to form the support of the medium to be optically analyzed. Since the light rays of the incident beam scatter as soon as they make progress in the support, a very fast attenuation of the light rays which tend to be optically guided by the support can be observed. This enables to strongly decrease, or even to bring down to zero, the proportion of light rays likely to be optically guided by the support all the way until they come out of it and directly reach the image sensor, or to be guided towards defects of the support which would behave as parasitic light sources.

Figure 4:
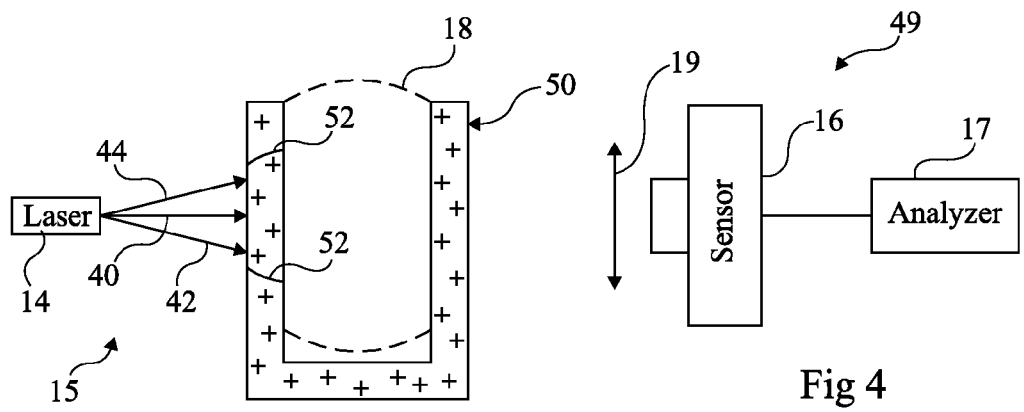
FIGS. 4 and 5 schematically show first and second examples of optical devices according to an embodiment of the present invention.

FIG. 4 shows an first embodiment of an optical device 49 according to the present invention. Optical device 49 comprises the same elements as device 12 shown in FIG. 3, except that it has a support 50 formed of a scattering material. Lines 52 schematically designate the diffusion region of incident light beam 15 reaching support 50. In the embodiment shown in FIG. 3, support 50 is tubular. However, support 50 may have another shape and, for example, comprise two parallel plates, in the same way as for optical device 10 shown in FIG. 1.

The support can also be applied against at least a part of a surface of a diffusing medium to be analyzed without necessarily containing or supporting the diffusing object to be analyzed in a given position. The aim is then to provide a diffusion of the incident light produced by a light source placed at a distance of the support, obtaining the advantages disclosed hereinafter. In such an arrangement, the support can be considered as a diffusing interface medium. Preferentially, the support will be in contact with the surface of the diffusing medium, so as to form with the diffusing medium a single diffusing set.

Figure 5:
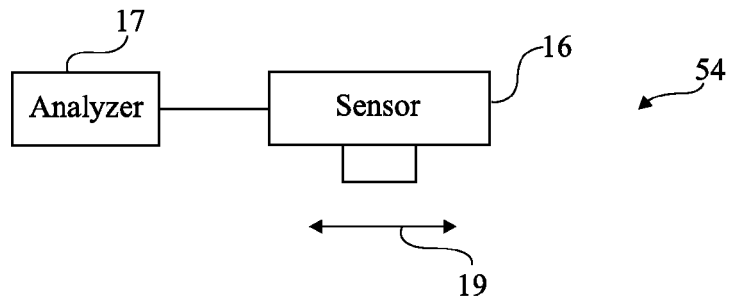
Figure 5:
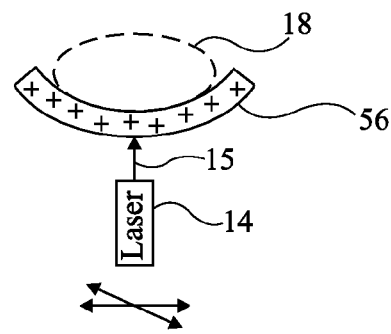

FIG. 5 shows a second embodiment of an optical device 54 according to the present invention. Optical device 56 comprises the same elements as device 10 shown in FIG. 3, except that it comprises a support 56 formed of a scattering material and having the shape of a cradle in which scattering medium 18 to be analyzed is placed. In the present embodiment, the shape of support 56 is advantageously adapted to scattering medium 18. This enables to decrease the possibilities of motion of the scattering medium during the analysis, in particular when the scattering medium is an animal or a human being.

The support being itself a scattering object, it forms with the scattering medium to be analyzed a scattering system having a precisely-known external surface, since it corresponds to the external surface of the support. Since this surface may correspond to a simple geometric shape, the resolution of the light propagation equations in scattering media can be simplified.

Another advantage of such a support is to produce a diffusion of the light produced by the incident beam before this light reaches the diffusing medium to be analyzed. The diffusion of the incident medium in the support provides a broadening of the surface of the diffusing medium impinged by this beam. Therefore, such a support reduces the light intensity per unit surface on the diffusing medium. The invention is particularly advantageous when the diffusing medium is a biologic medium, and the light source is a laser source providing a high intensity beam. In such a case, the incident beam, without a preliminary diffusion, could provide lesions such as burns at the surface of the analyzed diffusing medium. In the presence of the support disclosed here, the incident medium is diffused before attaining the surface of the diffusing medium, therefore reducing the risk of a lesion. It is thus possible to increase the intensity of the incident beam and, accordingly, the light quantity in the diffusing medium, due to the diffusion of the light before the surface of the diffusing medium.

Advantageously, to improve the optical coupling between the support and the scattering medium and thus ease the determination of a model of the propagation of light rays in the scattering system formed of the scattering support and of the scattering medium, the scattering and, further, absorption optical properties of the support may be selected to be close to those of the scattering medium to be analyzed. The reduced scattering coefficient $\mu'_s(sup)$ of the material forming the support is greater than 0.1 cm$^{-1}$ and, preferably, ranges between 1 and 700 cm$^{-1}$. The absorption coefficient $\mu'_a(sup)$ of the material forming the support may vary between 0 and 300 cm$^{-1}$ and, preferably, ranges between 0.01 and 300 cm$^{-1}$.

The support may be totally formed of a scattering and possibly absorbing medium. However, only one or several portions of the support may be formed of the scattering, and possibly absorbing, material, the rest of the support being formed of a substantially non-absorbing and non-scattering medium. The scattering portions are then advantageously provided at adapted locations of the support to avoid for optical guiding phenomena to cause the forming of artifacts on the images acquired by the image sensor. The support according to the present invention may be used with an optical device in which the scattering medium swims in an index-matching liquid.

The fact of using a scattering material to form the support enables to provide a low time-variation of the optical properties of the support. Indeed, to suppress the forming of artifacts on the images provided by the sensor of the optical device, a non-scattering support, some surfaces of which would have been frosted, could have been used. However, such a surface processing may be difficult to implement, especially when the support comprises non-planar portions. Further, the frosting may alter along time. In particular, the frosting may be damaged in shocks which result in defects at the support surface, causing the forming of artifacts on the images acquired by sensor 16.

Figure 6:
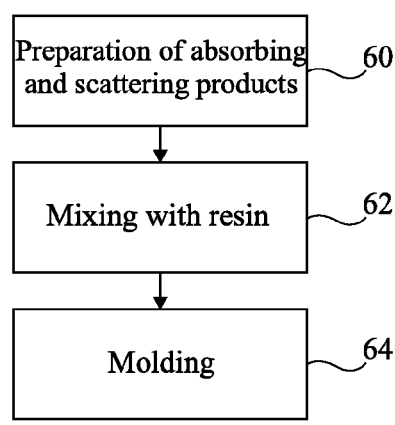
FIG. 6 shows, in the form of a block diagram, an example of a method for manufacturing a support of an optical device according to an embodiment of the present invention.

FIG. 6 shows in the form of a block diagram an example of a method for manufacturing a scattering support according to the present invention. In the present embodiment, both the scattering and absorption properties of the support are imposed. The scattering properties of the support are set by the addition of scattering particles, for example, titanium dioxide particles, to an initially non-absorbing and non-scattering material. The absorption properties of the support are set by the addition of an ink to the initial material, for example, an ink sold by Dabe Company under trade name Encre de Chine LOTUS. The initial material is, for example, a non-absorbing and non-scattering epoxy resin.

The method starts at step 60 with the preparation of the amount of ink and of the amount of titanium dioxide powder to be used. For this purpose, a reference absorbing solution containing ink diluted in ethanol may be used. Calling $V_T$ the resin volume to be used, volume $V_{ink}$ of the reference absorbing solution to be used to obtain the desired absorption coefficient $\mu_a(sup)$ is provided by the following relation:

$$V_{ink} = \frac{V_T \cdot \mu_a(sup)}{\mu_a(\text{ref})} \quad (1)$$

where $\mu_a(\text{ref})$ corresponds to the absorption coefficient of the reference absorbing solution. Coefficient $\mu_a(\text{ref})$ is, for example, previously measured by means of a spectrophotometer.

Calling $\mu'_s(sup)$ the decreased scattering coefficient of the support which is desired to be obtained, the mass m of titanium dioxide particles to be used is given by the following relation:

$$m = \frac{V_T \cdot C_{ref} \cdot \mu'_s(sup)}{\mu'_s(\text{ref})} \quad (2)$$

where $C_{ref}$ is the concentration of titanium dioxide particles in a reference scattering solution and $\mu'_s(\text{ref})$ is the decreased scattering coefficient obtained for said reference solution. The decreased scattering coefficient may be previously measured by diffuse reflectivity methods or by time-resolution methods, for example, the methods described in S. L. Jacques's publication entitled "Time-resolved reflectance spectroscopy in turbid tissues" (IEEE Transactions on biomedical engineering. 36, 1155-1161 (1989)).

As an example, a reference absorbing solution having an ink concentration of 1% with an absorption coefficient $\mu_a(\text{ref})$ for the 633-nm wavelength on the order of 30 cm$^{-1}$ and a reference scattering solution having a titanium dioxide concentration $C_{ref}$ of 10 mg/ml and for which the decreased scattering coefficient $\mu'_s(\text{ref})$ for the 633-nanometer wavelength which is on the order of 74 cm$^{-1}$ is considered. For a resin volume $V_T$ of 500 ml, and to obtain an absorption coefficient $\mu_a(sup)$ of 0.2 cm$^{-1}$ and a decreased scattering coefficient $\mu'_s(sup)$ of 10 cm$^{-1}$ for the 633-nanometer wavelength, relations (1) and (2) indicate that an ink volume $V_{ink}$ of 3.3 ml and a titanium dioxide mass m of 0.68 g must be used.

At step 60, volume $V_{ink}$ of the reference absorbing solution is sampled and the sampled volume is placed in a phial. Mass m of titanium dioxide is weighted and poured into the phial. The assembly may be placed in an ultrasound bath to help the elimination of possible clusters. The method carries on at step 62.

At step 62, the solution containing the ink and the titanium dioxide is mixed with resin volume $V_T$. A possibility is, in the case of a resin formed of a base and of a catalyst, to first mix the base and the catalyst and to wait a little before adding the solution containing the ink and the titanium dioxide. Another possibility is to incorporate the solution containing the ink and the titanium dioxide to the base and to add the catalyst of the resin afterwards. The phial containing the ink and the titanium dioxide may be rinsed with ethanol. The enclosure containing the resin-ink-titanium dioxide mixture is shaken to homogenize the mixture and may be placed in an ultrasound bath. The method carries on at step 64.

At step 64, the resin-ink-titanium dioxide mixture is placed in a mold adapted to the desired shape of the support. It is possible to let the resin polymerize at ambient temperature. After cooling and removal from the cast, a final support-machining step may be provided.

Such alterations, modifications, and improvements are intended to be part of this disclosure, and are intended to be within the spirit and the scope of the present invention. Accordingly, the foregoing description is by way of example only and is not intended to be limiting. The present invention is limited only as defined in the following claims and the equivalents thereto.

The invention claimed is:

1. An optical device configured to perform the analysis of diffused light emitted by a scattering medium, comprising:
   at least one light source distant from the scattering medium and capable of providing an incident light beam to illuminate the scattering medium;
   at least one sensor capable of detecting a radiation emitted by the scattering medium;
   a manufactured support of the scattering medium at least partially non-absorbing for the incident light beam and the scattered radiation, the incident light crossing the support before attaining the scattering medium,
   wherein all or part of the manufactured support is formed of a scattering material having a decreased scattering coefficient greater than 0.1 cm-1 and smaller than 700 cm-1.

2. The optical device of claim 1, wherein the scattering coefficient of the manufactured support ranges between 1 and 700 cm-1.

3. The optical device of claim 1, wherein said material has an absorption coefficient ranging between 0.01 and 300 cm-1.

4. The optical device of claim 1, wherein the diffusing medium of the manufactured support is selected so as to have diffusion and absorption optical properties close to the ones of the diffusing medium to be analyzed.

5. The optical device of claim 1, wherein the manufactured support comprises at least one wall located between the source and the scattering medium and/or between the scattering medium and the sensor.

6. The device of claim 1, wherein the manufactured support has the shape of a cradle configured to receive the scattering medium.

7. A manufactured support of a scattering medium adapted to an optical device configured to perform analysis of the scattering medium, and formed, entirely or partly, of a diffusion material having a decreased scattering coefficient greater than 0.1 cm-1 and smaller than 700 cm-1.

8. A method for forming by tomography a three-dimensional mapping of the absorption coefficient and/or of the decreased scattering coefficient of a scattering medium comprising
   providing an optical device comprising at least one light source distinct from the scattering medium, at least one sensor, a support of the scattering medium at least partially non-absorbing for the incident light beam and the scattered radiation, all the parts of the manufactured support being formed of a scattering material having a decreased scattering coefficient greater than 0.1 cm-1 and smaller than 700 cm-1;
   illuminating the scattering medium with an incident light beam provided by the light source, the incident light beam crossing the support before attaining the scattering medium; and
   detecting the radiation emitted by the scattering medium using the sensor.

9. A method for determining properties of fluorophores and/or properties of a scattering medium comprising:
   providing an optical device comprising at least one light source distinct from the scattering medium, at least one sensor, a manufactured support of the scattering medium at least partially non-absorbing for the incident light beam and the scattered radiation, all the parts of the support being formed of a scattering material having a decreased scattering coefficient greater than 0.1 cm-1 and smaller than 700 cm-1;
   placing the fluorophores in the scattering medium;
   illuminating the scattering medium with an incident light beam at a first wavelength provided by the light source, the incident light beam crossing the support before attaining the scattering medium, said fluorophores being sensitive to the first wavelength and emitting the scattered radiation at a second wavelength;
   detecting the radiation emitted by the scattering medium and the fluorophores using the sensor.

10. A method for manufacturing the manufactured support of claim 7, comprising the steps of:
    preparing a powder of a scattering material;
    mixing the powder with a solution of a substantially non-absorbing, non-scattering, and hardenable material; and
    injecting the obtained mixture into a mold to form the support.

11. The method of claim 10, further comprising the step of mixing an additional solution of an absorbing material with the powder or with the solution.

* * * * *

UNITED STATES PATENT AND TRADEMARK OFFICE
CERTIFICATE OF CORRECTION

PATENT NO. : 8,120,784 B2  
APPLICATION NO. : 12/425558  
DATED : February 21, 2012  
INVENTOR(S) : Da Silva et al.

Page 1 of 2

It is certified that error appears in the above-identified patent and that said Letters Patent is hereby corrected as shown below:

In the Abstract: Please replace "decreased scattering coefficient" with "reduced scattering coefficient"

In Column 2, Line 50-51: Please replace "decreased scattering coefficient" with "reduced scattering coefficient"

In Column 3, Line 2: Please replace "decreased scattering coefficient" with "reduced scattering coefficient"

In Column 6, Line 31: Please replace "decreased scattering coefficient" with "reduced scattering coefficient"

In Column 6, Line 41-42: Please replace "decreased scattering coefficient" with "reduced scattering coefficient"

In Column 6, Line 43: Please replace "decreased scattering coefficient" with "reduced scattering coefficient"

In Column 6, Line 54-55: Please replace "decreased scattering coefficient" with "reduced scattering coefficient"

In Column 6, Line 58-59: Please replace "decreased scattering coefficient" with "reduced scattering coefficient"

In Column 7, Line 38-39: Please replace "decreased scattering coefficient" with "reduced scattering coefficient"

In Column 8, Line 4: Please replace "decreased scattering coefficient" with "reduced scattering coefficient"

Signed and Sealed this  
Seventeenth Day of April, 2012

David J. Kappos  
*Director of the United States Patent and Trademark Office*

CERTIFICATE OF CORRECTION (continued)
U.S. Pat. No. 8,120,784 B2

In Column 8, Line 8: Please replace "decreased scattering coefficient" with "reduced scattering coefficient"

In Column 8, Line 16: Please replace "decreased scattering coefficient" with "reduced scattering coefficient"

In Column 8, Line 33: Please replace "decreased scattering coefficient" with "reduced scattering coefficient"

UNITED STATES PATENT AND TRADEMARK OFFICE
CERTIFICATE OF CORRECTION

PATENT NO. : 8,120,784 B2  
APPLICATION NO. : 12/425558  
DATED : February 21, 2012  
INVENTOR(S) : Anabela Da Silva et al.

Page 1 of 1

It is certified that error appears in the above-identified patent and that said Letters Patent is hereby corrected as shown below:

Title Page, Item (30) For. Appl. Priority Data.
Delete "08/82633" and insert -- 08/52633 --.

Signed and Sealed this
Twenty-ninth Day of May, 2012

David J. Kappos
*Director of the United States Patent and Trademark Office*